United States Patent [19]

Listemann et al.

[11] Patent Number: 5,117,056
[45] Date of Patent: May 26, 1992

[54] PREPARATION OF N-(1-ALKOXYALKYL)FORMAMIDE AND BIS FORMAMIDES

[75] Inventors: Mark L. Listemann, Whitehall; Robert K. Pinschmidt, Jr., Allentown, both of Pa.

[73] Assignee: Air Products and Chemicals, Inc., Allentown, Pa.

[21] Appl. No.: 631,597

[22] Filed: Dec. 21, 1990

[51] Int. Cl.$^5$ .............................. C07C 231/02
[52] U.S. Cl. ................... 564/134; 564/133; 564/139
[58] Field of Search ............. 564/133, 134, 187, 201, 564/205, 215, 224, 135, 139; 568/391, 671

[56] References Cited

U.S. PATENT DOCUMENTS

| | | | |
|---|---|---|---|
| 4,334,097 | 6/1982 | Schmidt | 564/201 |
| 4,504,422 | 3/1985 | Matsui et al. | 564/201 |
| 4,567,300 | 1/1986 | Murao et al. | 564/215 |
| 4,942,259 | 7/1990 | Parris et al. | 564/187 |

FOREIGN PATENT DOCUMENTS

| | | |
|---|---|---|
| 1273533 | 7/1968 | Fed. Rep. of Germany . |
| 1125940 | 9/1968 | United Kingdom . |
| 2152929A | 8/1985 | United Kingdom . |

OTHER PUBLICATIONS

Stackman, Robert W. and Summerville, Richard H. "Synthesis of N-Vinylacetamide and Preparation of Some Polymers and Copolymers" 24 Ind. Eng. Chem. Prod. Res. Dev. 242–246 (1985), vol. 24.

*Primary Examiner*—Glennon H. Hollrah
*Assistant Examiner*—S. Kumar
*Attorney, Agent, or Firm*—Russell L. Brewer; James C. Simmons; William F. Marsh

[57] ABSTRACT

This invention relates to an improved process for the formation of N-(1-alkoxyalkyl)amides with coproduction of alkylidene bisamides. The N-(1-alkoxyalkyl)formamides of this invention are prepared by reacting formamide with an acetal or hemiacetal carboxylate ester represented by the formulas:

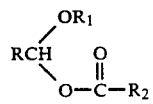

I

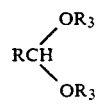

II wherein R is $C_1$–$C_8$ alkyl, aralkyl or aryl; $R_1$ and $R_2$ are $C_1$–$C_8$ alkyl, or aryl; and $R_3$ is secondary or tertiary alkyl having from 3–8 carbon atoms.

The reaction is carried out in the presence of an acid catalyst such as a strong acid ion exchange resin.

18 Claims, No Drawings

PREPARATION OF N-(1-ALKOXYALKYL)FORMAMIDE AND BIS FORMAMIDES

TECHNICAL FIELD

This invention relates to an improved process for the preparation of N-(1-alkoxyalkyl) formamides and alkylidene bisformamides which are precursors to N-alkenyl formamides which can be polymerized to form water-soluble homopolymers and copolymers.

BACKGROUND OF THE INVENTION

N-vinylamides have long been used as monomers for the production of homopolymers and copolymers having valuable properties. The polymer resulting from the polymerization of N-vinylamide contains reactive hydrogens which can be used as sites for effecting cross-linking attachment of activated substrates onto the polymer or the amide may be hydrolyzed to form polyvinylamine which is suitable for other uses.

Parris, et al. in U.S. Pat. No. 4,942,259 disclose catalytic processes for the cracking of N-(alkoxyalkyl)formamides and N-(alkoxyalkyl)amides as well as the corresponding bit-amides to produce the corresponding N-alkenyl amides. The N-alkenyl amides then can be polymerized. Of these, it is the N-(1-alkoxyethyl)formamides and bisformamides that lend themselves to the Parris, et al. catalytic cracking process to form N-vinylformamide; also it is the polymers formed from N-vinylformamide which can be more easily hydrolyzed than the polymers formed from an N-alkenylamide.

A number of routes for producing N-vinylcarboxylic amides have been suggested and these routes generally involve the production of either N-(alpha-alkoxyethyl)amides alternatively referred to as N-(1-alkoxyethyl)-carboxylic acid amides. Representative patents and articles which illustrate preparation of N-vinylamides are as follows: Stackman in U.S. Pat. No. 4,554,377 and in an article entitled *Synthesis of N-vinylacetamide and Preparation of Some Polymers and Copolymers*, 24 Ind. Eng. Chem. Prod. Res. Dev., 242–246 (1985), disclose the reaction of acetamide with dimethyl acetal to form the N-(alpha-alkoxyethyl)carboxylic acid amide. In this reaction there is a competing equilibrium reaction and this reaction involves the subsequent reaction of the N-(alpha-alkoxyethyl)carboxamide with another mole of alkylamide to form ethylidene-bis(alkylamide), an unwanted co-product. The reaction is carried out in the presence of an acid, such as methanesulfonic acid or sulfuric acid. When formamide was substituted for acetamide, the reaction was unsuccessful (p. 244).

Schmidt U.S. Pat. No. 4,334,097 discloses a process for producing N-(alpha-alkoxyalkyl)carboxamides by reacting primary and secondary carboxamides with an alpha-halogen alkyl ether. Tertiary amines are added to the reaction system to react with hydrogen halide as it is formed. The tertiary amine hydrogen halide then can be filtered from the reaction product and removed.

Bestian in German Patent 1,273,533 discloses a process for producing N-(alpha-alkoxyalkyl)carboxylic acid amides by reacting a secondary amide with acetals or hemiacetals. Representative acetals include those formed by the reaction of an aldehyde with primary and secondary alcohols, e.g., methanol, ethanol, isopropanol, and isobutanol. Acid catalysts including inorganic acids, such as, hydrochloric acid, acid chlorides, such as, sulfuryl chloride, and aromatic sulfonic acids and acid chlorides, such as, p-toluenesulfonic acid and chloride thereof are suggested as being suited for effecting reaction between the secondary carboxylic acid amide and acetal or hemiacetal.

N-(1-alkoxyethyl)carboxylic acid amides have been prepared by the electrochemical alkoxylation of N-ethylcarboxylic acid amides and by the reaction of formamide with aldehydes. In this regard Murao, et al. disclose in U.S. Pat. No. 4,567,300 and equivalent GB 2 152 929 a process wherein acetaldehyde reacts with formamide in the presence of a weakly basic catalyst to yield solid N-(1-hydroxyethyl)formamide which, following catalyst neutralization, reacts with alcohols in the presence of an acid catalyst to yield N-(1-alkoxyethyl)formamide. This process is unattractive in that it requires two discrete steps, the handling of a solid intermediate and the disposal of salts.

European Patent Publication 0 332,083 discloses the preparation of N-(1-alkoxyalkyl)carboxylic acid amides by reacting formamide with acetals derived from primary alcohols to produce the N-(1-alkoxyalkyl)formamide systems along with bisformamide. This reaction, in contrast to the statements made by Stackman, et al., is successful but requires the utilization of large amounts of acid in order to force the reaction of formamide with the acetal of a primary alcohol to form the N-(1-alkoxyalkyl)formamide.

SUMMARY OF THE INVENTION

This invention relates to an improved process for the preparation of N-(1-alkoxyalkyl)formamides involving the reaction of formamide with an acetal or hemiacetal ester in the presence of an acid catalyst. The improvement resides in the utilization of an acetal derived by the reaction of an aldehyde with a secondary or tertiary alkanol or alkoxy alkanol or hemiacetal carboxylate ester. The hemiacetal is represented by Formula I; the acetal is represented by Formula II.

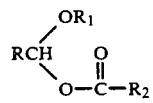

I

II wherein R is $C_1$–$C_8$ alkyl, aralkyl or aryl; $R_1$ and $R_2$ are $C_1$–$C_8$ alkyl, or aryl; and $R_3$ is secondary or tertiary alkyl having from 3–8 carbon atoms.

Numerous advantages, are achieved through the process of this invention which include:

the ability to obtain higher conversions of formamide to N-(1-alkoxyalkyl)formamide and at lower catalyst levels than reported heretofore; and the ability to minimize consumption of acid catalyst in achieving excellent conversion of formamide to N-(1-alkoxyalkyl)formamide.

DETAILED DESCRIPTION OF THE INVENTION

The preparation of N-(1-alkoxyalkyl)formamide is accomplished by the reaction of acetals and hemiacetal carboxylate esters described by the formulas recited above with a formamide. One type of acetal is formed by reacting an alkylaldehyde with a secondary or tertiary alcohol, or with an alkoxyalkanol having a secondary or tertiary alcohol group. Another is a hemiacetal ester formed by reacting an alkylaldehyde with an alcohol and alkylcarboxylic acid. Representative acetals and hemiacetal carboxylate esters include acetaldehyde diisopropyl acetal; acetaldehyde diisobutyl acetal; acetaldehyde ethyl isopropyl acetal; acetaldehyde isopropyl isobutyl acetal; isobutyraldehyde diisobutyl acetal; isobutyraldehyde diisopropyl acetal. Hemiacetal carboxylate esters include acetaldehyde ethyl hemiacetal acetate ester, acetaldehyde isopropyl hemiacetal acetate ester; acetaldehyde isobutyl hemiacetal acetate ester; acetaldehyde t-butylhemiacetal acetate ester and the like. Of the acetals, it is preferred that both of the acetal groups are derived from the same secondary or tertiary alcohol as distinguished from a mixed acetal where one of the R$_3$ groups is provided by primary alcohol and the other by a secondary or tertiary alcohol. In the case where hemiacetal carboxylate esters are used in the reaction with formamide, the corresponding carboxylic acid is generated as a byproduct.

The reaction of acetals derived from a primary alcohol and secondary alcohol or tertiary alcohol with formamide tends to be slightly worse than where both of the acetal groups are derived from secondary or tertiary alcohols. The use of an acetal having ether groups derived from a mixture of both primary and secondary alcohols also tends to create problems in separation and reduces conversion. In that regard they can have a negative effect upon the overall reaction performance.

Catalysts suited for effecting reaction between formamide and the acetal are acidic catalysts including those acids used in the prior art. These include inorganic acids, such as hydrochloric acid and sulfuric acid, aliphatic or aromatic sulfonic acids, such as methanesulfonic acid and p-toluenesulfonic acid; halogenated aliphatic acids, such as trifluoroacetic acid; and solid acid catalysts such as sulfonic acids carried in a fluorinated polymer network sold under the trademark Nafion or incorporated in macroreticular ion exchange resins sold under the trademark Amberlyst; and Lewis acids such as ferric chloride, tin tetrachloride, and aluminum trichloride. For ease of processing, the solid acid catalyst systems such as the ion exchange resins and solid phase catalysts are preferred for reasons of ease of separation from the reaction medium and ease of regeneration.

Temperatures suited for effecting reaction between formamide and the acetals range from about 0° to 200° C. with preferred temperatures ranging from 30°-50° C.

Pressures required for the reaction range from about atmospheric to autogenous. Under the reaction conditions generally specified, reaction times will range from about 1-24 hours with the reaction typically taking from about 2-4 hours.

The mole ratio of formamide to acetal derived from a secondary or tertiary alcohol, etc., may range from 0.5 to 4 moles:1 and preferably 2 to 3:1. When the mole ratio of formamide to acetal is increased above about 4:1, no significant advantages are seen and when the ratio falls below about 1:1, the selectivity with respect to acetal may suffer. In contrast to the prior art processes, the reaction of an acetal of a secondary or tertiary alcohol with formamide leads to the formation of high yields of N-(1-alkoxyalkyl)formamide and bisformamide at lower mole ratios of acetal to amide.

The catalyst is incorporated in the reaction within a range from about 0.01 to 0.1 moles based on moles acetal charged to the system. Although concentrations as high as 0.2 can be utilized, the excess acid seems to afford no significant advantages and in fact is deactivated much more quickly than at lower levels.

The reaction may be carried out neat or in a solvent and representative solvents include secondary and tertiary alkanols having from 1 to 8 carbon atoms, e.g., isopropanol, isobutanol, tert-butanol and so forth; acetonitrile, and high boiling ethers such as diisobutyl ether, dimethylglycol ether, tetraglyme, tetrahydrofuran and dioxane. There are essentially three criteria for the solvent, one is that it is capable of forming a single acetal/amide/solvent liquid phase; two it is not a good nucleophile with a reactive hydrogen; and, three the solvent is inert in the reaction medium.

EXAMPLE 1

Preparation of N-(1-isopropoxyethyl)formamide and Comparative Formamides

N-(1-isopropoxyethyl)formamide and related compositions were prepared in the conventional manner by reacting formamide with the appropriate acetal. More particularly, the reactants were charged to a stirred flask at which time a solid phase macroreticular ion exchange resin with sulfonic acid groups (Amberlyst 15) was added to provide preselected mole equivalents of acetal (m) per mole of formamide (n). At the completion of the reaction, the resin was filtered therefrom. The product was collected and analyzed.

Table 1 sets forth the reaction conditions and analysis of products including conversion based upon formamide charged.

TABLE 1

Comparison of Ethyl and Isopropyl Acetaldehyde Acetals m CH$_3$CH(OR)$_2$ + n H$_2$NCHO + x ROH 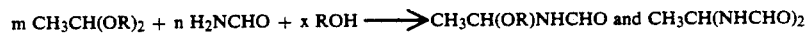 CH$_3$CH(OR)NHCHO and CH$_3$CH(NHCHO)$_2$

| Run | Mole %$^a$ Catalyst | R | Acetal (m) | Formamide (n) | Alcohol (x) | Temp (°C.) | Time (hrs) | % Yields$^a$ REF$^e$ | Bis$^f$ | Acetal$^b$ Conv (%) | Formamide$^b$ Conv (%) | Selectivity$^c$ (Acetal) | Selectivity$^d$ (Formamide) |
|---|---|---|---|---|---|---|---|---|---|---|---|---|---|
| 1 | 18 | Et | 2 | 1 | 0 | 80 | 2 | 59 | 7 | 40 | 91 | 83 | 81 |
| 2 | 18 | Et | 2 | 1 | 0 | 60 | 3 | 68 | 5 | 51 | 94 | 71 | 82 |
| 3 | 18 | Et | 1 | 1 | 0 | 25 | 4 | 45 | 3 | 61 | 74 | 79 | 70 |
| 4 | 10 | Et | 1 | 1.5 | 1 | 40 | 3 | 33 | 2 | 39 | 27 | 91 | 95 |
| 5 | 5 | i-Pr | 1 | 1 | 1 | 40 | 3 | 49 | 14 | 68 | 74 | 93 | 98 |
| 6 | 10 | i-Pr | 1 | 1 | 1 | 40 | 3 | 54 | 17 | 80 | 95 | 88 | 92 |
| 7 | 10 | i-Pr | 1 | 1.2 | 1 | 40 | 3 | 62 | 21 | 90 | 92 | 93 | 95 |
| 8 | 10 | i-Pr | 1 | 1.5 | 1 | 40 | 3 | 59 | 34 | 95 | 87 | 98 | 98 |

TABLE 1-continued
Comparison of Ethyl and Isopropyl Acetaldehyde Acetals m CH₃CH(OR)₂ + n H₂NCHO + x ROH ⟶ CH₃CH(OR)NHCHO and CH₃CH(NHCHO)₂

| Run | Mole %[a] Catalyst | R | Acetal (m) | Form-amide (n) | Alcohol (x) | Temp (°C.) | Time (hrs) | % Yields[a] REF[e] | Bis[f] | Acetal[b] Conv (%) | Formamide[b] Conv (%) | Selec-tivity[c] (Acetal) | Selectivity[d] (Formamide) |
|---|---|---|---|---|---|---|---|---|---|---|---|---|---|
| 9 | 10 | i-Pr | 1 | 2.0 | 1 | 40 | 3 | 55 | 39 | 96 | 72 | 98 | 93 |

[a]Mole % catalyst and % yields vs. the limiting reagent.
[b]Conversions expressed as a percentage of the initial reactant amount.
[c]Selectivity vs. acetal = [% yields (REF + Bis)/(Acetal conv. × m)] × 100.
[d]Selectivity vs. Formamide = [% yields (REF + 2 × Bis)/(formamide conv. × n) × 100
[e]REF = N-(1-alkoxyethyl)formamide, CH₃CH(OR)NHCHO.
[f]Bis = Ethylidene bisformamide, CH₃CH(NHCHO)₂.

Runs 1 and 2 demonstrate that high catalyst loadings (18 mole %) and an excess of the primary acetal, i.e., acetaldehyde ethyl acetal to formamide ratio (2:1 acetal) are required to obtain high formamide conversions with good selectivities. In this type of reaction, acetal recycle will be high, and large amounts of acid catalyst, which is completely deactivated during the run by stoichiometric reaction with formamide and alcohol, must be regenerated. Run 4 shows that addition of ethanol and lowering the acetal to amide ratio improves selectivity but further lowers conversion, it is believed this is because ethanol also causes rapid catalyst deactivation.

Run 8 shows that substitution of a hindered acetal derived from the secondary alcohol, isopropanol, for the primary acetal, acetaldehyde ethyl acetal, and substitution of isopropanol for ethanol as solvent, increases acetal conversion by a factor of 2.4, and increases formamide conversion by a factor of 3.2, under otherwise identical conditions. Refer to Run 4 for comparison. Thus, the acetaldehyde isopropyl acetal is substantially more efficient than acetaldehyde ethyl acetal in the reaction.

Runs 6–9 show that by increasing the formamide to acetal ratio from 1 to 2, one can increase acetal conversion from 80 to 95% while formamide conversion decreases from 95 to 72%. The formamide to acetal ratio of 1.5 affords high conversions of both reagents (run 8) while maintaining excellent selectivities. Thus, in contrast to prior art processes using high mole ratios of acetal to amide, it is not necessary to use an excess of acetal to formamide to obtain high formamide conversions and recycle of both reagents is minimized.

To summarize, the data show that the acetal formed by the reaction of an aldehyde with a secondary alcohol generates a faster reacting or leaving species than does the acetal formed by the reaction of an aldehyde with a compound having primary alcohol groups. The hemiacetal carboxylate ester appears to be even faster than the acetal formed with the secondary alcohol.

EXAMPLE 2

Effect of Solvent on Product Distribution and Catalyst Deactivation

The procedure of Example 1 was followed except that 3 different solvents, i.e. isopropanol (i-PrOH), tert-butanol (t-BuOH), and acetonitrile were utilized as solvents for the reaction. Table 2 below sets forth the reaction conditions including moles acetal, formamide, solvent, and results.

TABLE 2
Example 2. Effect of Solvent on Product Dist. and Catalyst Deactivation
0.10 Amberlyst 15

CH₃CH(O-i-Pr)₂ + 1.5 H₂NCHO + 1.0 solvent —40° C., 3h→ CH₃CH(OR)NHCHO and CH₃CH(NHCHO)₂

| Run # | Solvent | % Yields[a] i-PrEF[e] | Bis[f] | Alkyl Formate | Acetal[b] Conv (%) | Formamide[b] Conv (%) | Selectivity[c] (Acetal) | Selectivity[d] (Formamide) |
|---|---|---|---|---|---|---|---|---|
| 1 | i-PrOH | 59 | 34 | 3 | 95 | 87 | 98 | 98 |
| 2 | t-BuOH | 54 | 37 | 2 | 91 | 87 | 99 | 98 |
| 3 | CH₃CN | 56 | 41 | 2 | 93 | 89 | 100 | 98 |

[a]% yields vs. the limiting reagent, i-Pr acetal.
[b]Conversions expressed as a percentage of the initial reactant amount.
[c]Selectivity vs. acetal = [% yields (i-PrEF + Bis)/(Acetal conv.)] × 100.
[d]Selectivity vs. formamide = [% yields (REF + 2 × Bis)/(Formamide conv. × 1.5)] × 100
[e]i-PrEF = N-(1-isopropoxyethyl)formamide, CH₃CH(O-i-Pr)NHCHO.
[f]Bis = Ethylidene bisformamide, CH₃CH(NHCHO)₂.

Runs 1–3 show the impact of various alcohols and other solvents on catalyst deactivation. These particular solvents do not appear to significantly alter conversion or selectivity. Alkyl formate yield, a measure of catalyst deactivation, can be lowered from 3% (~33% of the original acid charged) to 2% (20% of the original acid) by replacing isopropanol with tert-butanol or acetonitrile. The tert-butanol reacts more slowly with the acid and formamide to cause deactivation, while acetonitrile does not react. Some deactivation is always observed because isopropanol is liberated during the course of the acetal/formamide reaction. Using solvents less reactive than isopropanol will lower catalyst deactivation to the minimum for this particular system.

EXAMPLE 3

Comparison of Acetal and Acetaldehyde/Alcohol Mixtures

The procedure of Example 1 was repeated except that the reaction of formamide with acetals formed in-situ from acetaldehyde and the corresponding alcohol (Runs 1 and 2) was compared to the corresponding reaction of the previously prepared acetals with formamide (Runs 3 and 4). Reactions 1–3 were carried out using 0.18 mole equivalents of Amberlyst 15 (A-15) ion exchange resin per mole of formamide using a reaction temperature of 25° and a reaction time of 4 hours. The pressure was atmospheric. Table 3 sets forth the reaction conditions and results.

EXAMPLE 4

Comparison of Acetal and Hemiacetal Carboxylic Acid Ester

The procedure of Example 1 was repeated, except that a hemiacetal carboxylic acid ester was substituted for the acetal. This reaction was also compared with the

TABLE 3

Comparison of Acetal and Acetaldehyde/Alcohol Mixtures

| Run # | R | % Yields$^a$ REF$^d$ | Bis$^e$ | Acetaldehyde or Acetal Conv (%) | Formamide Conv (%) | Selectivity$^b$ (Acetal) | Selectivity$^c$ (Formamide) |
|---|---|---|---|---|---|---|---|

$$CH_3CHO + 1.5\ ROH + H_2NCHO \xrightarrow{0.18\ A\text{-}15} CH_3CH(OR)NHCHO\ and\ CH_3CH(NHCHO)_2$$

| 1 | Et   | 58 | <1 | 66 | 87 | 88 | 67 |
| 2 | i-Pr | 40 | 10 | 49 | 85 | 97 | 71 |

$$CH_3CH(OEt)_2 + H_2NCHO \xrightarrow{0.18\ A\text{-}15} CH_3CH(OR)NHCHO\ and\ CH_3CH(NHCHO)_2$$

| 3 | Et | 45 | 3 | 61 | 74 | 79 | 70 |

0.05

$$CH_3CH(O\text{-}i\text{-}Pr)_2 + H_2NCHO + 1.0\ CH_3CN \xrightarrow{A\text{-}15} CH_3CH(OR)NHCHO\ and\ CH_3CH(NHCHO)_2$$

| 4 | i-Pr | 45 | 11 | 65 | 71 | 86 | 95 |

$^a$Mole % catalyst and % yields vs. the limiting reagent.
$^b$Conversions expressed as a percentage of the initial reactant amount.
$^c$Selectivity vs. acetal = [% yields (REF + Bis)/(Acetal conv.)] × 100.
$^d$Selectivity vs. formamide = [% yields (REF + 2 × Bis)/(Formamide conv.] × 100
$^e$REF = N-(1-alkoxyethyl)formamide, CH$_3$CH(OR)NHCHO.
$^f$Bis = Ethylidene bisformamide, CH$_3$CH(NHCHO)$_2$.

Runs 1 and 2 show the in situ reaction of either isopropanol or ethanol with acetaldehyde and formamide. Under these optimum in situ conditions using high acid levels, comparable conversions and selectivities are afforded. Reaction of the previously prepared ethyl acetal (Run 3) under the same conditions affords comparable results to the in situ reaction described in Runs 1 and 2. However, the reaction of the previously prepared i-Pr acetal, under comparable conditions to Runs 1 & 2, but with 3.6 times less catalyst, (Run 4) affords comparable conversions to those in Runs 1–3 and offers greatly improved formamide selectivity. In conclusion, the prepared i-Pr acetal is preferable to the use of an acetaldehyde/isopropanol mixture; the mixture does not appear to be equivalent to the preformed acetal in terms of conversion and selectivity.

The results are set forth in Table 4.

TABLE 4

$$CH_3CH(OR_1)(OR_2) + 1.5\ H_2NCHO + t\text{-}BuOH \longrightarrow CH_3CH(OR)NHCHO\ and\ CH_3CH(NHCHO)_2$$

| Entry No. | R$_1$ | R$_2$ | % Yields$^a$ REF$^e$ | Bis$^f$ | Alkyl Formate | Acetal or Ester$^b$ Conv (%) | Formamide$^b$ Conv (%) | Selectivity$^c$ Acetal | Selectivity$^d$ (Formamide) |
|---|---|---|---|---|---|---|---|---|---|
| 1 | Et | COCH$_3$ | 46 | 43 | 3 | 100 | 84 | 97 | 97 |
| 2 | Et | Et | 54 | 16 | 4 | 71 | 60 | 98 | 95 |
| 3 | i-Pr | i-Pr | 54 | 37 | 2 | 91 | 87 | 99 | 98 |

$^a$Mole % catalyst and & yields vs. the limiting reagent.
$^b$Conversions expressed as a percentage of the initial reactant amount.
$^c$Selectivity vs. acetal or ester = [% yields (REF + Bis)/(Acetal conv.)] × 100.
$^d$Selectivity vs. Formamide = [% yields (REF + 2 × Bis)/(Formamide conv. × 1.5)] × 100
$^e$REF = N-(1-alkoxyethyl)formamide, CH$_3$CH(OR)NHCHO.
$^f$Bis = Ethylidene bisformamide, CH$_3$CH(NHCHO)$_2$.

The acetate ester of ethyl acetaldehyde hemiacetal (Run 1, CH$_3$CH(OEt)(OCOCH$_3$)) because it incorporates an excellent leaving group affords excellent conversions, selectivities, and catalyst deactivation comparable to those obtained with i-Pr acetal (Run 3). The hemiacetal ester liberates acetic acid when it reacts with formamide, and the liberated acetic acid does not cause catalyst deactivation. Some catalyst deactivation still occurs with the hemiacetal ester because ethanol is liberated in a subsequent step to afford Bisformamide. Nonetheless, the benefits obtained from using a hemiacetal ester derived even from a primary alcohol are comparable and in some cases better than those obtained with acetals prepared only from secondary alcohols. The ethyl acetal (Run 2) is less satisfactory under otherwise identical conditions, because this acetal is less reactive, and it generates a primary alcohol which causes rapid catalyst deactivation.

COMMENTARY

In an effort to explain the benefits obtained from using an acetal derived from a secondary or tertiary alcohol or a hemiacetal carboxylate ester, the following is provided. Acetaldehyde diisopropyl acetal, $CH_3CH(O\text{-}i\text{-}Pr)_2$, an acetal derived in part by reacting acetaldehyde with the secondary alcohol, isopropanol, is sterically hindered, and thus loses isopropanol more readily than an unhindered primary acetal such as acetaldehyde diethyl acetal would lose ethanol. The steric hindrance provides a driving force for reaction which is seen experimentally in the lower catalyst loadings and temperatures required for the reaction with acetaldehyde diisopropyl acetal versus acetaldehyde diethyl acetal.

In a serious competing reaction, amides also react stoichiometrically with acids in the presence of water or alcohols as shown below (equation 1). The reaction of an amide with water forms the corresponding carboxylic acid and an amine salt of the strong acid catalyst $H^+X^-$. Neither the carboxylic acid nor the amine salt are sufficiently acidic to catalyze the desired reaction. Similarly, reaction of an amide and an acid in alcohol forms an ester and the amine salt of the acid catalyst (equation 2). If these reactions take place to a significant extent, the acid catalyst needed for the N-(1-alkoxyalkyl)amide synthesis is consumed and the selectivity is lowered due to consumption of the amide reactant.

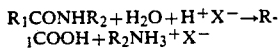

$$R_1CONHR_2 + H_2O + H^+X^- \rightarrow R_1COOH + R_2NH_3^+X^- \quad 1$$

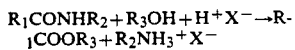

$$R_1CONHR_2 + R_3OH + H^+X^- \rightarrow R_1COOR_3 + R_2NH_3^+X^- \quad 2$$

The reactions set forth above aid in explaining the problems associated with the use of formamide and, to a lesser extent, other amides as a reactant with an acetal of a primary and an acetal of a secondary alcohol as well as with a hemiacetal carboxylate acid ester. For example, reaction 1 above proceeds at a faster rate than does reaction 2. However, both reactions 1 and 2 proceed at a faster rate when $R_1$ is hydrogen as in formamide than when $R_1$ is alkyl as in acetamide. When $R_1$ is hydrogen, both reactions proceed at a rate such that the acid catalyst and formamide are consumed before complete reaction of formamide with the acetal can take place. As a result selectivity to N-(1-alkoxyalkyl)-formamide and bis formamide, based on formamide charged, is poor when water is present or the alcohol is reactive with the amide. The examples also illustrate an additional advantage which is explained by reaction 2. Secondary and tertiary alcohols derived from acetals of secondary or tertiary alcohols, when released during the reaction between formamide and the acetal of a secondary or tertiary alcohol, will react more slowly with formamide and acid than will the corresponding primary alcohol when released.

Work described in prior art acetal/amide chemistry has supported the contention that acetal and aldehyde/alcohol mixtures are equivalent. This is expected because the acetal $CH_3CH(OR)_2$ or hemiacetal $CH_3CH(OR)(OH)$ both generate the key intermediate $CH_3CH=OR+$ in the presence of acid. However, it appears that if the acetal is derived from secondary or tertiary alcohols, the steric strain provides an additional driving force to generate the key intermediate; this driving force is not present in the hemiacetal or the acetal of a primary alcohol. Example 3 shows that $CH_3CHO/i\text{-}PrOH$ mixtures are no better than $CH_3CHO/EtOH$ mixtures (Runs 2 and 1, respectively), because water is generated in the reaction and this deactivates the catalyst.

To summarize:

Sterically hindered acetals and hemiacetal esters have higher reactivity with formamide, which allows lower catalyst loadings and reaction temperatures, and minimizes recycle; and two Sterically hindered secondary and tertiary alcohols or carboxylic acids deactivate the acid catalyst much more slowly in the presence of formamide than primary alcohols or water.

What is claimed is:

1. In a process for the preparation of N-(alkoxyalkyl)amides and alkylidene bisamides wherein an alkylamide is reacted with an ether containing composition in the presence of an acid catalyst to form said N-(alkoxyalkyl)amide, the improvement for producing N-(1-alkoxyalkyl)formamides and alkylidene bisformamides which comprises reacting formamide with an acetal or hemicetal carboxylate ester represented by the formulas:

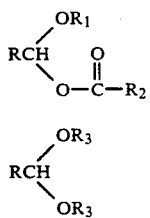

wherein R is $C_1$–$C_8$ alkyl, hydrocarbyl aralkyl or hydrocarbyl aryl; $R_1$ and $R_2$ are $C_1$–$C_8$ alkyl, or hydrocarbyl aryl; and $R_3$ is secondary or tertiary alkyl having from 3–8 carbon atoms.

2. The process of claim 1 wherein the ether containing acetal-type composition is represented by Formula II and R is methyl.

3. The process of claim 2 wherein $R_3$ is isopropyl.

4. The process of claim 2 wherein $R_3$ is t-butyl.

5. The process of claim 3 wherein a solvent is used and the solvent is tert-butanol.

6. The process of claim 3 wherein the mole ratio of formamide to acetal is from 0.5 to 4:1.

7. The process of claim 1 wherein the acetal-type composition is represented by Formula I and R is methyl.

8. The process of claim 7 wherein $R_1$ is ethyl.

9. The process of claim 7 wherein $R_1$ is isopropyl.

10. The process of claim 1 wherein $R_1$ is tert-butyl.

11. The process of claim 8 wherein $R_2$ is ethyl or methyl.

12. The process of claim 9 wherein $R_2$ is ethyl or methyl.

13. The process of claim 10 wherein $R_2$ is ethyl or methyl.

14. The process of claim 9 wherein $R_2$ is isopropyl.

15. The process of claim 10 wherein $R_2$ is isopropyl.

16. The process of claim 10 wherein $R_2$ is tert-butyl.

17. The process of claim 7 wherein $R_1$ is methyl and $R_2$ is methyl.

18. The process of claim 7 wherein $R_1$ is methyl and $R_2$ is ethyl, isopropyl or tert-butyl.

* * * * *